US008426628B2

(12) United States Patent
Just et al.

(10) Patent No.: US 8,426,628 B2
(45) Date of Patent: Apr. 23, 2013

(54) PROCESS FOR PREPARING ALKYLAMINOALKYLALKOXYSILANES

(75) Inventors: Eckhard Just, Rheinfelden (DE); Philipp Albert, Lörrach (DE); Peter Jenkner, Wesel (DE)

(73) Assignee: Evonik Degussa GmbH, Essen (DE)

( * ) Notice: Subject to any disclaimer, the term of this patent is extended or adjusted under 35 U.S.C. 154(b) by 117 days.

(21) Appl. No.: 12/995,852

(22) PCT Filed: Apr. 17, 2009

(86) PCT No.: PCT/EP2009/054587
§ 371 (c)(1),
(2), (4) Date: Feb. 3, 2011

(87) PCT Pub. No.: WO2009/146971
PCT Pub. Date: Dec. 10, 2009

(65) Prior Publication Data
US 2011/0118496 A1    May 19, 2011

(30) Foreign Application Priority Data

Jun. 3, 2008    (DE) .......................... 10 2008 002 182

(51) Int. Cl.
*C07F 7/10* (2006.01)
(52) U.S. Cl.
USPC ............................ 556/462; 556/458; 556/478
(58) Field of Classification Search .................. 556/478, 556/413, 437, 443, 462, 458
See application file for complete search history.

(56) References Cited

U.S. PATENT DOCUMENTS

| | | | |
|---|---|---|---|
| 5,616,755 A * | 4/1997 | Seiler et al. .................. 556/413 |
| 5,698,726 A | 12/1997 | Rauleder et al. | |
| 6,150,551 A | 11/2000 | Kropfgans et al. | |
| 6,177,584 B1 | 1/2001 | Loewenberg et al. | |
| 6,423,858 B1 * | 7/2002 | Schwarz et al. .............. 556/413 |
| 6,696,587 B2 | 2/2004 | Jenkner | |
| 6,750,361 B2 | 6/2004 | Kropfgans et al. | |

FOREIGN PATENT DOCUMENTS

| | | | |
|---|---|---|---|
| DE | 101 40 563 | | 2/2003 |
| DE | 10140563 | * | 2/2003 |
| EP | 0 702 017 | | 3/1996 |

OTHER PUBLICATIONS

International Search Report issued Sep. 2, 2009 in PCT/EP09/054587 filed Apr. 17, 2009.
U.S. Appl. No. 12/988,637, filed Oct. 20, 2010, Albert, et al.
U.S. Appl. No. 12/995,871, filed Dec. 2, 2010, Albert, et al.
U.S. Appl. No. 05/971,966, filed Dec. 21, 1978, Kappler, et al.
U.S. Appl. No. 10/246,525, filed Sep. 19, 2002, Kahsnitz, et al.
U.S. Appl. No. 13/062,225, filed Mar. 4, 2011, Weissenbach, et al.

* cited by examiner

*Primary Examiner* — Johann Richter
*Assistant Examiner* — Pancham Bakshi
(74) *Attorney, Agent, or Firm* — Oblon, Spivak, McClelland, Maier & Neustadt, L.L.P.

(57) ABSTRACT

A process for preparing an alkylamino-alkylalkoxysilane of formula (I) R—(NR')—Y—Si($R^1$)$_n$(O$R^2$)$_{3-n}$ (I) in which R is a linear, branched or cyclic alkyl group having 1 to 12 carbon atoms, R' is a hydrogen (H) or is a linear, branched or cyclic alkyl group having 1 to 12 carbon atoms, Y is a bivalent alkyl group from the group of —$CH_2$—, —$(CH_2)_2$—, —$(CH_2)_3$—, —$(CH_2)(CH(CH_3))(CH_2)$— and —$(CH_2)_4$—, $R^1$ and $R^2$ groups are the same or different and are each a linear or branched alkyl group having 1 to 4 carbon atoms, and n is 0 or 1 or 2, by reacting an alkylamine, used in excess, distilling off excess free alkylamine, treating the remaining product mixture with the alkylaminoalkylalkoxysilane and working up.

20 Claims, No Drawings

PROCESS FOR PREPARING ALKYLAMINOALKYLALKOXYSILANES

The present invention relates to a process for preparing alkylaminoalkylalkoxysilanes by reacting an alkylamine with a haloalkylalkoxysilane, then working up the resulting product mixture and recycling the alkylamine into the process.

It is known that alkylaminoalkylalkoxysilanes, such as Dynasylan® 1189, a 3-(n-butylamino)propyltriethoxysilane, can be prepared by reacting a corresponding alkylamine with a haloalkylalkoxysilane (DE 101 40 563). The reaction forms hydrogen halide, for example hydrogen chloride (HCl), which reacts both with the alkylamine generally used in excess and with the product formed in the reaction, the alkylaminoalkylalkoxysilane, to give the corresponding amine hydrohalides. The amine hydrohalides are partly dissolved in the product and are transferred to a crystallizer for precipitation. The crystallizer is cooled and optionally operated at a lower pressure level than that of the preceding reaction stage. The amine hydrohalide precipitated in the crystallizer is removed from the crude product by filtration, and the pure product is obtained by distillation. It is disadvantageous that the removal of the amine hydrochlorides removes both alkylamine used in the form of alkylamine hydrohalide and product in the form of alkylaminoalkylalkoxysilane hydrohalide. This leads to product loss compared to the theoretically expected yield. Moreover, reactant is lost in the form of the corresponding aminoalkyl hydrohalide, which is additionally at the expense of the economic viability of the process. Furthermore, the amine hydrohalides removed have to be disposed of or recovered in usually complex processes.

It was an object of the present invention to find a means of alleviating abovementioned disadvantages. More particularly to provide a process in which a minimum amount of residue to be disposed of arises, and which enables a high yield.

The object was achieved in accordance with the invention according to the information in the claims.

For instance, the reaction of an alkylamine, for example n-butylamine, with a haloalkylalkoxysilane, for example 3-chloropropyltrimethoxysilane, can advantageously be performed advantageously in a simple stirred apparatus, as in a paddle drier or stirred tank, without an additional crystallizer, to achieve high yields. Moreover, after the reaction of the alkylamine used in excess with the haloalkylalkoxysilane has ended, free alkylamine can be distilled off. The resulting product mixture comprises alkylamine hydrohalide and alkylaminoalkylalkoxysilane hydrochloride, and can advantageously be distilled further with addition of an alkylaminoalkylalkoxysilane corresponding to the compounds present, in which case the addition of appropriate amounts of alkylaminoalkylalkoxysilane in particular also allows the residual alkylamine to be released from the alkylamine hydrochloride present in the product mixture and removed by distillation.

For instance, it is possible in a comparatively simple manner to recover the alkylamine used in excess to an extent of more than 90% and recycle it back into the process, which advantageously contributes to the particular economic viability of the present process. In the bottoms of the distillation stage remains an alkylaminoalkylalkoxysilane hydrohalide corresponding to the product.

For advantageous workup of the product or product hydrohalide mixture thus obtained,
the product or product hydrohalide mixture is heat treated, reacted with an alkali metal alkoxide solution, alkali metal halide is precipitated and removed, and the solvent of the alkali metal alkoxide solution used is removed from the product by distillation to obtain the product,
or
a nonpolar organic solvent is added to the product or product hydrohalide mixture, the mixture is treated with an aqueous alkali metal or alkaline earth metal hydroxide solution, the resulting aqueous phase comprising metal salt is separated from the organic product phase, and the organic phase is distilled to obtain the product.

The present invention therefore provides a process for preparing an alkylaminoalkylalkoxysilane of the general formula I

$$R-(NR')-Y-Si(R^1)_n(OR^2)_{3-n} \quad (I)$$

in which R is a linear, branched or cyclic alkyl group having 1 to 12 carbon atoms, R' is a hydrogen (H) or a linear, branched or cyclic alkyl group having 1 to 12 carbon atoms, Y is a bivalent alkyl group from the group of —CH$_2$—, —(CH$_2$)$_2$—, —(CH$_2$)$_3$—, —(CH$_2$)(CH(CH$_3$))(CH$_2$)— and —(CH$_2$)$_4$—, $R^1$ and $R^2$ groups are the same or different and are each a linear or branched alkyl group having 1 to 4 carbon atoms, and n is 0 or 1 or 2, by
reacting an alkylamine of the general formula II used in excess

$$R(NR')H \quad (II)$$

in which R is a linear, branched or cyclic alkyl group having 1 to 12 carbon atoms and R' is a hydrogen (H) or a linear, branched or cyclic alkyl group having 1 to 12 carbon atoms with a haloalkylalkoxysilane of the general formula III

$$X-Y-Si(R^1)_n(OR^2)_{3-n} \quad (III)$$

in which X is Cl or Br, Y is a bivalent alkyl group from the group of —CH$_2$—, —(CH$_2$)$_2$—, —(CH$_2$)$_3$—, —(CH$_2$)(CH(CH$_3$))(CH$_2$)— and —(CH$_2$)$_4$—, $R^1$ and $R^2$ groups are the same or different and are each a linear or branched alkyl group having 1 to 4 carbon atoms, and n is 0 or 1 or 2, distilling off excess free alkylamine,
at the same time, i.e. during the aforementioned distillation, treating the remaining product mixture comprising alkylamine hydrohalide and alkylaminoalkylalkoxysilane hydrohalide with addition of an alkylaminoalkylalkoxysilane corresponding to the present compounds, removing the alkylamine released as a result from the system and
working up the remaining product or product hydrohalide mixture.

Preference is given to performing the reaction in a heatable and coolable stirred apparatus resistant to elevated pressure and reduced pressure, which simultaneously offers a distillation means. Advantageously, the apparatus may be equipped with an additional means of phase separation.

In the process according to the invention, the alkylamine is used relative to the haloalkylalkoxysilane advantageously in a molar ratio of 1.1:1 to 10:1, preferably of 1.5:1 to 10:1, more preferably of 1.8:1 to 6:1, even more preferably of 2:1 to 5:1, especially of 4:1.

For instance, the alkylamine of the formula II used in the process according to the invention is preferably methylamine, ethylamine, n-propylamine, n-butylamine, 2-heptylamine, 2-butylamine, n-pentylamine, 2-pentylamine, 3-pentylamine, n-hexylamine, n-heptylamine, octylamine, 2-octylamine, nonylamine, decylamine, undecylamine or dodecylamine.

Additionally preferably, the haloalkylalkoxysilane of the formula III used in the process according to the invention is 3-chloropropyltrimethoxysilane, 3-chloropropyltriethoxysilane, 3-chloroisobutyltrimethoxysilane, 3-chloroisobutyltriethoxysilane, 2-chloroethyltrimethoxysilane, 2-chloroethyltriethoxysilane, 1-chloromethyltrimethoxysilane, 1-chloromethyltriethoxysilane, chloropropylmethyldimethoxysilane, chloropropylmethyldiethoxysilane, chloropropyldimethylmethoxysilane, chloropropyldimethylethoxysilane, chloroisobutylmethyldimethoxysilane, chloroisobutyldimethylmethoxysilane, chloroisobutyldimethylethoxysilane, chloroisobutyldimethyldiethoxysilane, chloroethylmethyldimethoxysilane, chloroethylmethyldiethoxysilane, chloroethyldimethylmethoxysilane, chloroethyldimethylethoxysilane, chloromethylmethyldimethoxysilane, chloromethylmethyldiethoxysilane, chloromethyldimethylmethoxysilane or chloromethyldimethylethoxysilane.

To perform the process according to the invention, the alkylamine and the haloalkylalkoxysilane are added with good mixing to the reaction apparatus intended therefor, in the course of which the temperature of the reaction mixture generally rises. To conduct the reaction, the apparatus can, if required, be cooled or heated, and the internal pressure can be varied. The reaction mixture can be mixed by means of suitable stirring, mixing or kneading devices. For instance, the reaction is suitably performed at a temperature of 60 to 200° C., preferably of 60 to 180° C., more preferably of 60 to 130° C., and a pressure of 0.1 to 20 bar, preferably of 0.1 to 5 bar. The reaction has generally ended after 30 minutes to 16 hours, preferably after 1 to 15 hours, more preferably between 2 and 14 hours. Thereafter, excess alkylamine is conducted out of the system, suitably by a distillation, in which case an alkylaminoalkylalkoxysilane corresponding to the product is added in a well-defined amount in accordance with the invention, such that the alkylamine is released from the amount of alkylamine hydrohalide still present in the product mixture by shifting the equilibrium, and the alkylaminoalkylalkoxysilane supplied is correspondingly converted to alkylaminoalkylalkoxysilane hydrohalide.

For workup, the product or product hydrohalide mixture thus obtained can be reacted at just the right temperature, i.e. in a soft stirrable or pasty miscible state, with an alkali metal alkoxide solution, which precipitates alkali metal halide which is removed from the product, for example, in a simple and economically viable manner by filtration. Subsequently, the solvent of the alkali metal alkoxide solution used can be removed from the product, for example by distillation, and the product can be supplied to a purifying distillation. The particular distillation steps can be performed in a thin-film or short-path evaporator and/or in a distillation column. Part of the product stream can be reused advantageously in the process for the above-described release of alkylamine from alkylamine hydrochloride.

In the process according to the invention, the workup can also be performed in such a way that
  the present product or product hydrohalide mixture is mixed with an essentially nonpolar organic solvent, preferably selected from the group of hexane, heptane, octane, cyclohexane, especially toluene,
  the resulting mixture is treated and allowed to react with an aqueous alkali, preferably over a defined period, cf. also reaction equation below,
  then the aqueous phase is separated from the organic phase, and
  the organic solvent is removed from the organic phase to obtain the remaining organic phase.

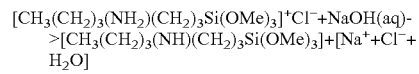

[CH$_3$(CH$_2$)$_3$(NH$_2$)(CH$_2$)$_3$Si(OMe)$_3$]$^+$Cl$^-$+NaOH(aq)->[CH$_3$(CH$_2$)$_3$(NH)(CH$_2$)$_3$Si(OMe)$_3$]+[Na$^+$+Cl$^-$+H$_2$O]

The aqueous alkali used may preferably be a strong alkali having a pH of at least 12, more preferably 13 to 14. The pH can be determined in a manner known per se to the person skilled in the art, for example by means of pH paper. The alkali used is preferably an NaOH or KOH solution. The concentration of the aqueous alkali can be selected such that the aqueous phase after the workup reaches a pH of 12. pH values above 12 are preferable. The mixture thus obtained is suitably allowed to react while stirring for up to 30 minutes, preferably 10 seconds to 10 minutes, more preferably 15 seconds to 5 minutes, even more preferably 20 seconds to 3 minutes, especially 30 seconds to 1 minute. Preference is given to performing the aqueous workup at a temperature in the range from 5 to 100° C., more preferably from 10 to 60° C. and most preferably in the range from 20 to 40° C. It is advantageously possible to work in a heatable/coolable stirred tank with a conically tapering bottom, including bottom outlet and viewing window. The tank and stirrer are preferably made from a non-rusting material, for example stainless steel or enameled steel. In general, two phases form after only a short rest time, which are present with a sharp separation from one another. After the formation of the two phases, the aqueous phase can be discharged from the organic phase via the bottom valve of the tank and thus separated from the organic phase. The aqueous phase generally contains the salt formed in the reaction in dissolved form; in the case of use of sodium hydroxide solution, the aqueous phase thus comprises, for example, dissolved NaCl. The organic phase can then be transferred into a separating unit, for example into a distillation, or be conducted through a thin-film evaporator or through a short-path evaporator. It is possible to remove organic solvent present there, suitably by removal under reduced pressure. In the bottoms remains the organic phase, which is suitably filtered and/or distilled to obtain the product.

In a preferred embodiment of the process according to the invention, n-butylamine is introduced with 3-chloropropyltrimethoxysilane (CPTMO) in a molar ratio of 3 to 1 into a stirred tank, for example a stirred autoclave, allowed to react with good mixing (also referred to as "reaction" for short) at a temperature of 60 to 180° C. and a pressure of 0.1 to 10 bar, and then excess n-butylamine is distilled out of the reactor, preferably at 105 to 115° C., for example according to:

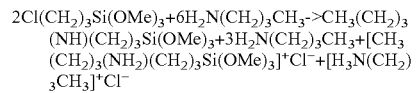

2Cl(CH$_2$)$_3$Si(OMe)$_3$+6H$_2$N(CH$_2$)$_3$CH$_3$->CH$_3$(CH$_2$)$_3$(NH)(CH$_2$)$_3$Si(OMe)$_3$+3H$_2$N(CH$_2$)$_3$CH$_3$+[CH$_3$(CH$_2$)$_3$(NH$_2$)(CH$_2$)$_3$Si(OMe)$_3$]$^+$Cl$^-$+[H$_3$N(CH$_2$)$_3$CH$_3$]$^+$Cl$^-$

During the distillative removal of the free n-butylamine, butylamine hydrochloride can react with n-butylaminopropyltrimethoxysilane (Dynasylan® 1189) present, and optionally added according to the ratios present, to give n-butylamine and 3-(trimethoxysilyl)-N-(n-butyl)propylamine hydrochloride. Thus, at the start of the distillation, both the n-butylamine and the 3-(n-butylamino)propyltrimethoxysilane are present only partly in protonated form, i.e. as hydrohalides. The distillation removes n-butylamine from the system, which shifts the equilibrium to 3-(trimethoxysilyl)-N-(n-butyl)propylamine hydrochloride:

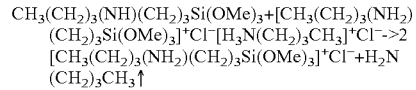

CH$_3$(CH$_2$)$_3$(NH)(CH$_2$)$_3$Si(OMe)$_3$+[CH$_3$(CH$_2$)$_3$(NH$_2$)(CH$_2$)$_3$Si(OMe)$_3$]$^+$Cl$^-$[H$_3$N(CH$_2$)$_3$CH$_3$]$^+$Cl$^-$->2[CH$_3$(CH$_2$)$_3$(NH$_2$)(CH$_2$)$_3$Si(OMe)$_3$]$^+$Cl$^-$+H$_2$N(CH$_2$)$_3$CH$_3$↑

A reaction of n-butylamine with CPTMO with a ratio of 3:1 consumes 1 mol of n-butylamine. 2 moles of n-butylamine can be removed again by distillation without any addition. This is because the reaction forms 1 mol of HCl, and, as a result of the distillation, 1 mol of n-butylaminopropylsilane hydrochloride is present at the end of the reaction.

In a reaction of n-butylamine with CPTMO, however, corresponding "bis-silylamine" [N-butyl-N,N-bis(trimethoxysilylpropyl)amine] is also obtained as a by-product.

Thus, the reaction consumes less n-butylamine, and hence less n-butylaminopropylsilane which can absorb HCl is available in the distillation. It is thus advantageous to add n-butylaminopropyltrimethoxysilane, for example at the end of the distillation. This allows the n-butylamine to be obtained virtually completely.

In addition, methanol (MeOH) can be recovered after the removal of salts via an azeotrope composed of MeOH and n-butylamine.

In the process according to the invention, it is advantageously possible to recover about 93 to 99% of the excess n-butylamine, for example in a purity of 98%, and to reuse it in the next reaction.

3-(Trimethoxysilyl)-N-(n-butyl)propylamine hydrochloride is soft and pasty at about 75° C. The product can be released in a simple and economically viable manner from the product hydrohalide [3-(trimethoxysilyl)-N-(n-butyl)propylamine hydrochloride] obtained after distillation at a temperature of about 70° C. by means of a sodium methoxide solution, preferably 30% by weight of sodium methoxide in methanol:

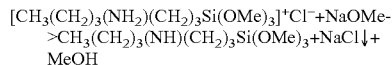

The NaCl which precipitates out in the course thereof, or after the composition has been cooled, can be filtered off, for example, through a Supra 500 filter plate. The filtercake is generally free-flowing and has only a low residual moisture content. The methanol can be removed from the product at 34 to 93° C. and a pressure of 200 mbar. In addition, the product, 3-(n-butylamino)propyltrimethoxysilane, can be purified further by a distillation at a bottom temperature of 93 to 146° C. and a pressure of <1 mbar. For instance, the distillation can be effected using a distillation column, a column system, a thin-film evaporator or short-path evaporator, or a combination of the aforementioned possibilities.

Particularly advantageously, 3-(n-butylamino)propyltrimethoxysilane or 3-(n-butylamino)propyltriethoxysilane can be obtained as the product by the process according to the invention.

The present invention is illustrated in detail by the examples which follow, without restricting the subject matter.

EXAMPLES

Example 1

Reaction in a 5 l Stirred Autoclave with Distillation Apparatus

A nitrogen-blanketed stirred autoclave was initially charged with 1878.8 g (25.7 mol) of n-butylamine. At a bottom temperature of 79° C. (oil bath temperature 90° C.) and a pressure of 0.5 bar, 1719.6 g (8.6 mol) of Dynasylan® CPTMO (3-chloropropyltrimethoxysilane) were metered in with a metering pump within 1.5 hours. In the course of this, the temperature rose from 79° C. to 89° C.; the pressure fell to 0.4 bar. For further reaction, the mixture was then stirred at 100-102° C. and a pressure of 0.5 bar for 13 hours, in the course of which the pressure fell from 0.5 bar to 0.2 bar after 2 hours.

GC Composition after the Reaction:

| | |
|---|---|
| CH$_3$OH: | 0.8 GC TCD area % |
| CH$_3$(CH$_2$)$_3$NH$_2$: | 29.1 GC TCD area % |
| 3-(n-Butylamino)propyltrimethoxysilane: | 62.6 GC TCD area % |
| High boilers: | 5.8 GC TCD area % |

Removal of n-Butylamine:

The distillation was started at 74° C. and 400 mbar, and the pressure was lowered gradually to 200 mbar.

A total of 1211.8 g of butylamine (16.2 mol) were obtained with a purity of 97.7%. n-Butylamine yield: 95%

Release of the Aminoalkylalkoxysilane with Sodium Methoxide Solution:

After the distillation of the n-butylamine, the bottom temperature was reduced to 75° C., and 1608.5 g of a 30% sodium methoxide solution were added. Subsequently, the mixture was stirred at about 70° C. for 1 hour.

After cooling to 25° C., the mixture was discharged and filtered in a 10 l pressurized suction filter at a pressure of 0.6 bar through a Supra500 filter plate. The filtercake was washed with 600 g (3×200 g) of methanol.

| | |
|---|---|
| Weight of NaCl: | 534.4 g |
| Weight of filtrate: | 3795.7 g (filtrate additionally contained 600 g of wash methanol) |

Distillation

At a bottom temperature of 34° C. to 93° C. and a pressure of 200 mbar, the first runnings were collected within approx. 2 hours. After the collection of the first runnings, the pressure was reduced gradually to <1 mbar and the bottom temperature was increased to 108° C. (boiling). At a bottom temperature of 93-146° C. and a pressure of <1 mbar, the product was collected.

| | |
|---|---|
| First runnings: | 1643.9 g including wash methanol (91% methanol, 9% n-butylamine) |
| Main fraction: | 1643.9 g [purity: 97.7% n-butylaminopropyltrimethoxysilane] |
| Residue: | 230 g |

Example 2

A nitrogen-blanketed 1 l Büchi stirred autoclave was initially charged with 219.3 g (=3 mol) of n-butylamine (BTA). At a bottom temperature of 129° C. (oil bath temperature=166° C.) and a pressure of 3.2 bar gauge, 199.0 g (=1.0 mol) of 3-chloropropyltrimethoxysilane were metered in with a metering pump within 1 hour. In the course of this, the temperature rose from 129° C. to 157° C., and the pressure rose at first to 4.2 bar gauge. After the metered addition had ended, the pressure fell to 3.0 bar gauge. For further reaction, the mixture was stirred at 150 to 157° C. and a pressure of 2.9 bar gauge for 4 hours, in the course of which the pressure fell from 2.9 bar to 2.1 bar after 1 hour. Subsequently, the n-butylamine was condensed out of the reactor via a distillation apparatus into a receiver flask within 15 minutes. In the course of this, the absolute pressure fell to 1.0 bar. On attainment of absolute pressure 1.0 bar, the pressure was lowered slowly to 63 mbar at a bottom temperature of 143° C., and the n-butylamine was removed from the receiver flask.

The absolute pressure was reduced to <1 mbar, and the residual n-butylamine was condensed out in a cooled receiver. A total of 143 g of n-butylamine were obtained.

| | | GC TCD area % | | | |
|---|---|---|---|---|---|
| Product | Mass [g] | Methanol | n-Butyl-amine | 3-Chloropropyl-trimethoxy-silane | n-Butyl-aminopropyl-trimethoxy-silane | Re-main-der |
| Butyl-amine fraction | 143 | 1.1 | 97.8 | 0.2 | 0.2 | 0.7 |

Evaluation of n-Butylamine (BTA) Recovery:

| Weight of BTA: | 143 g, purity 97.8% |
|---|---|
| Theoret. amount of BTA: | 149 g |
| BTA yield: | 94% |

Release of the Silane with Sodium Methoxide Solution and Filtration:

On attainment of a bottom temperature of 75° C., 187 g of 30% sodium methoxide solution were added and the mixture was stirred at about 70° C. for 1 hour.

After cooling, the mixture was discharged and filtered in a 2 l pressurized suction filter through a Supra500 filter plate at a pressure of 0.6 bar. The filtration took a few minutes. Subsequently, the filtercake was washed with 210 g (3×70 g) of methanol.

Weight of NaCl=62 g
Weight of filtrate=441 g (filtrate additionally contains 210 g of wash methanol)
GC Composition of Filtrate:

| Methanol = | 47% |
|---|---|
| n-Butylamine = | 3% |
| n-Butylaminopropyltrimethoxysilane = | 44% |
| N,N-Bis[triethoxysilylpropyl]butylamine = | 4% |
| Residue = | 2% |

Distillation of n-Butylaminopropyltrimethoxysilane:

At a bottom temperature of 34 to 93° C., a top temperature of 30 to 40° C. and a pressure of 200 mbar, the first runnings are collected. In order to collect the main fraction, the pressure was lowered gradually to <1 mbar and the bottom temperature increased to 108° C. (boiling). At a bottom temperature of 93 to 146° C., a top temperature of 98 to 108° C. and a pressure of <1 mbar, the n-butylaminopropyltrimethoxysilane main fraction was collected.

| First runnings (92% methanol, 8% n-butylamine) = | 324 g |
|---|---|
| Main fraction (n-butylaminopropyltrimethoxysilane)= | 200 g |
| Residue = | 27 g |
| n-Butylaminopropyltrimethoxysilane yield = | 85% |

Example 3

A nitrogen-blanketed 1 l Büchi stirred autoclave was initially charged with 220 g=3 mol of n-butylamine (BTA). At a bottom temperature of 130° C. (oil bath temperature=165° C.) and a pressure of 3.2 bar gauge, 199.0 g (=1.0 mol) of 3-chloropropyltrimethoxysilane were metered in with a metering pump within 1 hour. In the course of this, the temperature rose from 130° C. to 157° C. and the pressure rose at first to 4.5 bar gauge. After the metered addition had ended, the pressure fell to 3.0 bar gauge. For further reaction, the mixture was stirred at 150° C. and a pressure of 3 bar gauge for 4 hours, in the course of which the pressure fell from 3 to 2.1 bar after 1 hour. Subsequently, the n-butylamine was condensed out of the reactor via a distillation apparatus into a receiver flask within 15 minutes. In the course of this, the absolute pressure fell to 1.0 bar. On attainment of absolute pressure 1.0 bar, 20 g (=0.08 mol) of n-butylaminopropyltrimethoxysilane were added at a bottom temperature of 138° C., and the pressure was lowered gradually to an absolute pressure of 65 mbar. Subsequently, the n-butylamine was removed from the receiver flask. The absolute pressure was reduced to <1 mbar and the remaining n-butylamine was condensed out in a cooled receiver. A total of 148 g of butylamine were obtained.

| | | GC TCD area % | | | |
|---|---|---|---|---|---|
| Product | Mass [g] | MeOH | Butyl-amine | 3-Chloropropyl-trimethoxy-silane | n-Butylamino-propyl-trimethoxy-silane | Re-main-der |
| Butyl-amine fraction | 148 | 0.6 | 98.7 | 0.1 | 0.3 | 0.3 |

Evaluation of N-Butylamine (BTA) Recovery:

| Weight of BTA: | 148 g, purity 98.7% |
|---|---|
| Theoret. amount of BTA: | 149 g |
| BTA yield: | 98% |

Release of the Silane with Sodium Methoxide Solution and Filtration:

On attainment of a bottom temperature of 75° C., 187 g of 30% sodium methoxide solution were added and the mixture was stirred at about 70° C. for 1 hour.

After cooling, the mixture was discharged and filtered in a 2 l pressurized suction filter through a Supra500 filter plate at a pressure of 0.6 bar. The filtration took a few minutes. Subsequently, the filtercake was washed with 210 g (3×70 g) of methanol.

| Weight of NaCl = | 65 g |
|---|---|
| Weight of filtrate = | 450 g (filtrate additionally contains 210 g of wash methanol) |
| Methanol = | 48% |
| n-Butylamine = | 1% |
| n-Butylaminopropyltrimethoxysilane = | 45% |
| N,N-Bis[triethoxysilylpropyl]butylamine = | 4% |
| Residue = | 2% |

9

GC Composition of Filtrate:
Distillation of n-Butylaminopropyltrimethoxysilane:
At a bottom temperature of 35 to 95° C., a top temperature of 30 to 40° C. and a pressure of 200 mbar, the first runnings are collected. In order to collect the main fraction, the pressure was lowered gradually to <1 mbar and the bottom temperature was increased to 108° C. (boiling). At a bottom temperature of 93 to 146° C., a top temperature of 98 to 108° C. and a pressure of <1 mbar, the main fraction of DS 1189 was collected.

| | |
|---|---|
| First runnings (92% methanol, 8% n-butylamine) = | 330 g |
| Main fraction (n-butylaminopropyltrimethoxysilane) = | 225 g |
| Residue = | 20 g |
| n-Butylaminopropyltrimethoxysilane yield = | 87% |

Example 4

328.95 g (4.5 mol) of n-butylamine were initially charged in a 1 l Büchi glass autoclave. At a temperature of 130° C. and a pressure of 3.2 bar, 298.5 g (1.5 mol) of CPTMO were metered in by means of a pump (5 ml/min). After the metered addition had been ended, the reaction was kept at 155° C. for 2 h, then cooled to 140° C. After the reactor had been decompressed, the n-butylamine was removed by distillation at 145° C. The crystal slurry was admixed with 1295 g of toluene and transferred while warm to a separating funnel. Then a cold aqueous solution (93 g of NaOH and 270 g of H$_2$O) was added and mixed vigorously for 30 s. The subsequent phase separation took 30 s.

| | |
|---|---|
| Weight of aqueous phase: | 413 g |
| Weight of organic phase: | 1609 g |

The organic phase was freed of the toluene on a rotary evaporator at 89 to 95 mbar and 57 to 65° C. Subsequently, the product was distilled at 3 mbar and 126° C.
1st fraction (toluene): 1217 g
2nd fraction (product): 271.9 g of clear colorless liquid
Yield: 72%

The invention claimed is:
1. A process for preparing an alkylaminoalkylalkoxysilane of formula I

$$R—(NR')—Y—Si(R^1)_n(OR^2)_{3-n} \quad (I),$$

wherein
R is a linear, branched, or cyclic alkyl group having 1 to 12 carbon atoms,
R' is a hydrogen (H) or a linear, branched, or cyclic alkyl group having 1 to 12 carbon atoms,
Y is a bivalent alkyl group selected from the group consisting of —CH$_2$—, —(CH$_2$)$_2$—, —(CH$_2$)$_3$, —(CH$_2$)(CH(CH$_3$))(CH$_2$)—, and —(CH$_2$)$_4$—,
R$^1$ and R$^2$ groups are the same or different and are each a linear or branched alkyl group having 1 to 4 carbon atoms, and
n is 0, 1, or 2,
the method comprising:
(A) reacting an alkylamine of formula II, in excess, $$R(NR')H \quad (II),$$

wherein R is a linear, branched, or cyclic alkyl group having 1 to 12 carbon atoms, and

10

R' is a hydrogen (H) or a linear, branched or cyclic alkyl group having 1 to 12 carbon atoms,
with a haloalkylalkoxysilane of formula III $$X—Y—Si(R^1)_n(OR^2)_{3-n} \quad (III),$$

wherein
X is Cl or Br,
Y is a bivalent alkyl group selected from the group consisting of —CH$_2$—, —(CH$_2$)$_2$—, —(CH$_2$)$_3$—, —(CH$_2$)(CH(CH$_3$))(CH$_2$)—, and —(CH$_2$)$_4$—,
R$^1$ and R$^2$ groups are the same or different and are each a linear or branched alkyl group having 1 to 4 carbon atoms, and
n is 0, 1, or 2;
(B) distilling off excess alkylamine from a remaining product mixture;
(C) at the same time, adding the alkylaminoalkylalkoxysilane to the remaining product mixture, comprising alkylamine hydrohalide and alkylaminoalkylalkoxysilane hydrohalide, and removing the alkylamine released as a result from the mixture, to give a remaining product or product hydrohalide mixture and
(D) working up the remaining product or product hydrohalide mixture.
2. The process according to claim 1, wherein the working up (D) comprises:
heat treating;
reacting with an alkali metal alkoxide solution;
precipitating and removing alkali metal halide formed, to give a product solution; and
removing solvent introduced with the alkali metal alkoxide solution from the product solution by distillation to obtain the alkylaminoalkylalkoxysilane.
3. The process according to claim 1, wherein the working up (D) comprises:
adding a nonpolar organic solvent;
treating the mixture with an aqueous alkali metal or alkaline earth metal hydroxide solution, to give a resulting aqueous phase comprising metal salt and an organic phase;
separating the resulting aqueous phase containing metal salt from the organic product phase; and
distilling the organic phase to obtain the alkylaminoalkylalkoxysilane.
4. The process according to claim 1, wherein the alkylaminoalkylalkoxysilane obtained is recycled partly into the process to release the corresponding alkylamine from the alkylamine hydrohalide.
5. The process according to claim 1, wherein alkylamine recovered is recycled as a reactant component.
6. The process according to claim 1, wherein the alkylamine of formula II is methylamine, ethylamine, n-propylamine, n-butylamine, 2-heptylamine, 2-butylamine, n-pentylamine, 2-pentylamine, 3-pentylamine, n-hexylamine, n-heptylamine, octylamine, 2-octylamine, nonylamine, decylamine, undecylamine, or dodecylamine.
7. The process according to claim 1, wherein the haloalkylalkoxysilane of formula III is 3-chloropropyltrimethoxysilane, 3-chloropropyltriethoxysilane, 3-chloroisobutyltrimethoxysilane, 3-chloroisobutyltriethoxysilane, 2-chloroethyltrimethoxysilane, 2-chloroethyltriethoxysilane, 1-chloromethyltrimethoxysilane, 1-chloromethyltriethoxysilane, chloropropylmethyldimethoxysilane, chloropropylmethyldiethoxysilane, chloropropyldimethylmethoxysilane, chloropropyldimethylethoxysilane, chloroisobutylmethyldimethoxysilane, chloroisobutyldimethylmethoxysilane, chloroisobutyldimethylethoxysilane, chloroisobutyldimethyldiethoxysilane, chloroethylmethyldimethoxysilane, chloroethylmethyldiethoxysilane, chloroethyldimethylmethoxysilane, chloroethyldimethylethoxysilane, chloromethylmethyldimethoxysilane, chloromethylmethyldiethoxysilane, chloromethyldimethylmethoxysilane, or chloromethyldimethylethoxysilane.

8. The process according to claim 1, wherein the alkylamine and the haloalkylalkoxysilane are present in the reacting (A) in a molar ratio of 1.1:1 to 10:1.

9. The process according to claim 1, wherein the reacting is performed at a temperature of 60 to 200° C. and a pressure of 0.1 to 20 bar, and over a duration of 30 minutes to 16 hours.

10. The process according to claim 1, wherein the alkylaminoalkylalkoxysilane obtained is 3-(n-butylamino)propyltrimethoxysilane or 3-(n-butylamino)propyltriethoxysilane.

11. The process according to claim 2, wherein the alkylaminoalkylalkoxysilane obtained is recycled partly into the process to release the corresponding alkylamine from the alkylamine hydrohalide.

12. The process according to claim 3, wherein the alkylaminoalkylalkoxysilane obtained is recycled partly into the process to release the corresponding alkylamine from the alkylamine hydrohalide.

13. The process according to claim 2, wherein alkylamine recovered is recycled as a reactant component.

14. The process according to claim 3, wherein alkylamine recovered is recycled as a reactant component.

15. The process according to claim 4, wherein alkylamine recovered is recycled as a reactant component.

16. The process according to claim 11, wherein alkylamine recovered is recycled as a reactant component.

17. The process according to claim 12, wherein alkylamine recovered is recycled as a reactant component.

18. The process according to claim 2, wherein the alkylamine of formula II is methylamine, ethylamine, n-propylamine, n-butylamine, 2-heptylamine, 2-butylamine, n-pentylamine, 2-pentylamine, 3-pentylamine, n-hexylamine, n-heptylamine, octylamine, 2-octylamine, nonylamine, decylamine, undecylamine, or dodecylamine.

19. The process according to claim 3, wherein the alkylamine of formula II is methylamine, ethylamine, n-propylamine, n-butylamine, 2-heptylamine, 2-butylamine, n-pentylamine, 2-pentylamine, 3-pentylamine, n-hexylamine, n-heptylamine, octylamine, 2-octylamine, nonylamine, decylamine, undecylamine, or dodecylamine.

20. The process according to claim 4, wherein the alkylamine of formula II is methylamine, ethylamine, n-propylamine, n-butylamine, 2-heptylamine, 2-butylamine, n-pentylamine, 2-pentylamine, 3-pentylamine, n-hexylamine, n-heptylamine, octylamine, 2-octylamine, nonylamine, decylamine, undecylamine, or dodecylamine.

* * * * *